(12) United States Patent
Sumrall et al.

(10) Patent No.: US 8,230,916 B2
(45) Date of Patent: *Jul. 31, 2012

(54) APPARATUS AND METHODS TO ANALYZE DOWNHOLE FLUIDS USING IONIZED FLUID SAMPLES

(75) Inventors: Ernest N. Sumrall, Houston, TX (US); Anthony Goodwin, Sugar Land, TX (US); Erik Quam, Missouri City, TX (US); Chengli Dong, Sugar Land, TX (US); Oliver C. Mullins, Ridgefield, CT (US)

(73) Assignee: Schlumberger Technology Corporation, Sugar Land, TX (US)

( * ) Notice: Subject to any disclaimer, the term of this patent is extended or adjusted under 35 U.S.C. 154(b) by 489 days.

This patent is subject to a terminal disclaimer.

(21) Appl. No.: 12/246,039

(22) Filed: Oct. 6, 2008

(65) Prior Publication Data

US 2009/0126928 A1 May 21, 2009

Related U.S. Application Data

(60) Provisional application No. 60/988,703, filed on Nov. 16, 2007.

(51) Int. Cl.
*E21B 49/08* (2006.01)
(52) U.S. Cl. .................. 166/250.01; 73/152.55; 166/66; 356/436

(58) Field of Classification Search ............. 166/250.01, 166/66; 175/59; 73/152.55, 152.11; 356/70, 356/241.1, 436; 250/269.1
See application file for complete search history.

(56) References Cited

U.S. PATENT DOCUMENTS

| 5,902,939 | A | 5/1999 | Ballard et al. |
| 7,084,392 | B2 | 8/2006 | DiFoggio et al. |
| 7,733,490 | B2 * | 6/2010 | Goodwin et al. ............. 356/436 |
| 2004/0000636 | A1 | 1/2004 | Mullins et al. |
| 2004/0045706 | A1 | 3/2004 | Pop et al. |
| 2006/0243033 | A1 | 11/2006 | Freemark et al. |
| 2006/0243047 | A1 | 11/2006 | Terabayashi et al. |
| 2007/0068242 | A1 | 3/2007 | DiFoggio |
| 2007/0143023 | A1 | 6/2007 | Betancourt et al. |
| 2009/0126928 | A1 | 5/2009 | Sumrall et al. |

FOREIGN PATENT DOCUMENTS

| WO | WO01/20322 | 3/2001 |
| WO | WO01/73424 | 10/2001 |
| WO | WO2005/017316 | 2/2005 |

* cited by examiner

*Primary Examiner* — Hoang Dang
(74) *Attorney, Agent, or Firm* — David J. Smith

(57) ABSTRACT

Apparatus and methods to analyze downhole fluids are described herein. A disclosed example method involves obtaining a sample of a downhole fluid. Additionally the example method involves ionizing at least a portion of the sample to decompose molecules having a relatively high molar mass into molecules having a relatively lower molar mass. Further, the example method involves analyzing the ionized portion of the sample to determine a parameter of the downhole fluid sample.

28 Claims, 12 Drawing Sheets

432

| ATOM/ MOLECULE IDENTIFIER | REFERENCE PARAMETER MEASUREMENT VALUES | | | IONIZATION ENERGY EXPOSURE DURATION | IONIZATION ENERGY LEVEL |
|---|---|---|---|---|---|
| | NON-IONIZED SAMPLE | IONIZED SAMPLE | RATIO | | |
| | | | | | |
| | | | | | |
| | | | | | |
| | | | | | |
| | | | | | |

502 — ATOM/MOLECULE IDENTIFIER
504 — REFERENCE PARAMETER MEASUREMENT VALUES
506 — IONIZATION ENERGY EXPOSURE DURATION
508 — IONIZATION ENERGY LEVEL
510 — NON-IONIZED SAMPLE
514 — IONIZED SAMPLE
516 — RATIO

FIG. 5

APPARATUS AND METHODS TO ANALYZE DOWNHOLE FLUIDS USING IONIZED FLUID SAMPLES

CROSS-REFERENCE TO RELATED APPLICATIONS

This patent claims priority to U.S. Provisional Patent Application No. 60/988,703, filed on Nov. 16, 2007, which is hereby incorporated herein by reference in its entirety. This patent is also related to U.S. patent application Ser. No. 12/246,107, now issued as U.S. Pat. No. 7,733,490, entitled "APPARATUS AND METHODS TO ANALYZE DOWNHOLE FLUIDS USING IONIZED FLUID SAMPLES," filed on Oct. 6, 2008 concurrently herewith.

BACKGROUND OF THE DISCLOSURE

Drilling, completion, and production of reservoir wells involve measuring various subsurface formation parameters. Companies often measure percentages of oil, water, and gas mixtures contained in representative fluid samples drawn from formations to determine fluid composition or fluid quality. A detailed description of the fluid properties and characteristics is desirable for an accurate modeling of the fluids in the formation and to determine the economic value of pumping from the formation.

Historically, fluid samples were brought to the surface for analysis in a laboratory, but recent developments have facilitated directly measuring fluid properties downhole during a pumping or sampling sequence using downhole fluid analysis (DFA) techniques. In contrast to laboratory analyses or surface wellsite analyses, which may require a relatively extended amount of time to produce results and may result in undesirable phase transitions as well as the loss of key constituents in samples, DFA techniques may be used to perform fluid analysis in situ and to provide analysis results in real-time.

A known technique for determining the characteristics of a formation fluid often involves performing a spectroscopic analysis at a particular wavelength to measure an optical response of the formation fluid indicative of the presence of a molecule. A spectrometer is relatively accurate in determining the fluid properties and characteristics of molecules with relatively low molecular mass. However, determining the fluid properties and characteristics of molecules with relatively higher molecular masses (or molar masses) is significantly more difficult because they are more difficult or impossible to detect and/or differentiate between using known fluid analysis techniques. For example, using a spectrometer to measure fluids having molecules with relatively higher molecular masses (or molar masses) often produces inaccurate and/or invalid results.

SUMMARY OF THE DISCLOSURE

In accordance with a disclosed example, an example method of analyzing a downhole fluid involves obtaining a sample of a downhole fluid. Additionally, the example method involves measuring a first parameter of the sample in a non-ionized state, ionizing at least a portion of the sample to decompose molecules having a relatively high molar mass into molecules having a relatively lower molar mass, and measuring the ionized portion of the sample to determine a second parameter. A property of the downhole fluid is determined from the first and second parameters.

In accordance with another disclosed example, an example apparatus to analyze a downhole fluid includes an ionizer to ionize at least a portion of a sample of the downhole fluid and to decompose molecules in the at least the portion of a sample having a relatively high molar mass into molecules having a relatively lower molar mass, a fluid measurement unit to measure a characteristic of the sample of the downhole fluid, and a fluid measurement unit to measure a characteristic of the at least ionized portion of the sample. Additionally, the example apparatus includes a processing unit configured to determine a parameter of the downhole fluid based on the characteristic of the sample and the characteristic of the at least ionized portion of the sample.

BRIEF DESCRIPTION OF THE DRAWINGS

FIG. 5 is an example reference database that may be used to store reference measurement data of fluids having known fluid components and fluid component concentrations.

DETAILED DESCRIPTION

Certain examples are shown in the above-identified figures and described in detail below. In describing these examples, like or identical reference numbers are used to identify the same or similar elements. The figures are not necessarily to scale and certain features and certain views of the figures may be shown exaggerated in scale or in schematic for clarity and/or conciseness.

Generally, formation fluids having relatively higher molecular mass (or molar mass) have relatively large hydrocarbon chains that are typically not visible to and/or detectable by traditional downhole fluid analysis systems. Using a spectrometer (e.g. an optical spectrometer, an NMR spectrometer, etc.) for determining the fluid properties and characteristics of molecules with relatively higher molecular masses (or molar masses) is significantly more difficult, in part, due to their chemical complexity and the inability of the spectrometer to distinguish between the higher molecular mass (or molar mass) molecules. For example, this difficulty may arise because the spectral absorption lines associated with the modes of rotation, of vibration, etc. . . . blur into each in an optical spectra as the fluid density increases. In particular, the absorption spectra of these molecules overlap in the same wavelength region. Accordingly, difficulties may arise when using spectrometers to measure fluids having molecules with molecular masses (or molar masses) higher than, for example, $C_5H_{12}$ of molar mass $M=0.0721498$ kg·mol$^{-1}$. Specifically, as molecular mass (or molar mass) increases, the precision of measurements of these molecules obtained by a spectrometer decrease because of the overlap in the spectra. In general, as the number of carbon atoms increases, known fluid analysis techniques provide decreasing certainty and ultimately invalid results.

The example methods and apparatus described herein can be used to analyze fluids from a subsurface formation or a wellbore using breakdown techniques for fragmenting molecules present in the analyzed downhole fluid. In particular, the example methods and apparatus described herein can be used to perform fluid analyses of formation fluids having relatively higher molecular mass (or molar mass) and that are typically invisible to or undetectable by traditional fluid analysis systems. The example methods and apparatus described herein to analyze formation fluids involve obtaining a fluid sample, analyzing the sample using a downhole fluid analysis (DFA) technique, ionizing the sample (e.g., to breakdown larger hydrocarbon chains into smaller hydrocarbon chains, etc.), and analyzing the ionized fluid sample using the DFA technique. While the analyses described herein may be done substantially downhole, the analyses may alternatively be performed partially downhole and partially up-hole (i.e., at ground level), or up-hole (e.g., at a wellsite, in a laboratory, etc.).

Figure 4:
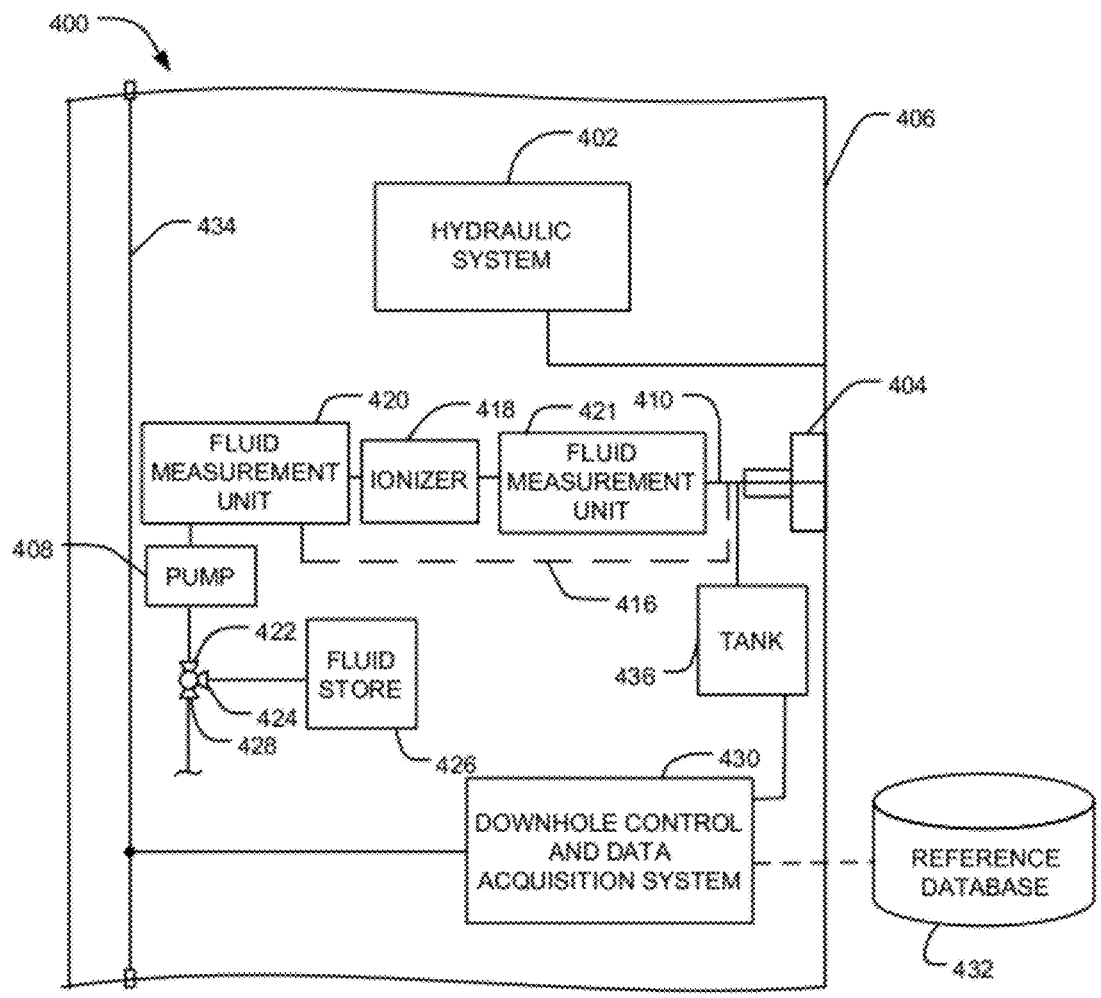
FIG. 4 depicts a block diagram of an example apparatus that may be used to implement a formation tester in the example tools of FIGS. 1, 2, and/or 3 to analyze formation fluid samples.

In the illustrated examples described herein, fluid samples can be ionized by moving the samples through an ionization chamber and exposing the samples to an ionizing energy such as, for example, an ultraviolet energy, a lightwave emission, a near infrared (NIR) radiation, etc. In some example implementations described herein, an ionizing lightwave emission source (e.g., an ultraviolet light source) is used to ionize a formation fluid sample to induce particle breakdowns of higher molecular mass (or molar mass) hydrocarbons into lower molecular mass (or molar mass) hydrocarbons by breaking the hydrocarbon chains into smaller species, such as smaller hydrocarbon chains, which can be resolved using fluid analysis techniques that can detect the smaller species. In general, the ionizing radiation provides sufficient energy to break the bonds of the molecules. Typically, the energy required to break these bonds is relatively lower for molecules of higher molar mass. Once the larger hydrocarbon chains have been broken into smaller hydrocarbon chains, the fragmented molecules (e.g., the smaller hydrocarbon chains) or free radicals react to form other molecules, having usually a lower energy state. In particular, the ionizing radiation initiates the breaking of chemical bonds including carbon-carbon bonds and, thus, the chemical composition of the formation fluid changes from the original composition by free radial reactions. It should be appreciated however that the breakdown process may reduce the molar mass of the formed molecules, or increase it, or keep it constant but form a different isomer. The molecules formed will depend on the collisions in the fluid and the rate of these collisions or in other words the mean free path the fragmented molecules or free radicals. Thus, the formation fluid density and viscosity, amongst other things, may play a role in the breakdown mechanism and may advantageously be measured before ionization, or reduced using a solvent provided in the tank 436 (FIG. 4).

After breaking down hydrocarbon chains in this manner, fluid analysis techniques such as, for example, optical fluid analysis (OFA) techniques can be performed using a spectrometer to relatively accurately identify chemical species, analyte(s), molecules, substances, and/or fluid components (e.g., methane, ethane, propane, etc.) in fluid samples and the concentrations of those species, analyte(s), molecules, substances, or fluid components. For example, optical absorption at particular wavelengths may indicate the presence of particular species in a fluid sample. In addition to identifying the chemical species and/or analyte(s) present within the fluid samples and/or determining the compositions of fluid samples, the example methods and apparatus described herein can also be used to measure density and viscosity of non-ionized samples and/or ionized samples. Specifically, the viscosity of an ionized sample may change due at least in part to newly generated hydrocarbons of lower molar mass and/or of different spatial configuration that may for example tend to approximate spheres.

To determine initial compositions (e.g., compositions data related to larger chains) of measured fluid samples before the molecular breakdown or decomposition, the concentration of larger chains is inverted at least in part from measured properties (e.g. measured concentrations into smaller chains) in accordance with model(s) of a molecular decomposition process(es). In particular, the measurements of the fluid samples after ionization can be compared to reference measurements stored in a reference database of ionized formation fluid samples having known fluid component compositions and component concentrations. The reference database can store the fluid measurements after ionization of the reference fluid samples in association with respective known fluid composition data and known component concentration data before ionization. The reference database can then, for example, be used to identify one or more reference fluids or a mixture thereof having measurements values or a combination thereof similar to measurement values subsequently obtained with downhole formation fluid samples ionized using the example methods and apparatus described herein. The known fluid component compositions and component concentrations of the identified reference fluid(s) are in turn used to determine initial compositions (e.g., compositions data related to larger chains) of the downhole fluid samples before the molecular breakdown or decomposition.

Optionally, measurements of non-ionized fluid samples may be used in addition of measurements of ionized samples. In particular, the measurements of the fluid samples before ionization can also be compared to reference measurements stored in a reference database. In some example implementations, relationships (e.g. ratios, differences, etc.) between the measurements of non-ionized samples and the samples after ionization can be compared to relationships of reference measurements stored in the reference database to identify the larger hydrocarbon chains within a fluid sample and their concentrations.

The reference database may include laboratory data collected in, for example, a laboratory environment using similar ionizing techniques to measure reference formation fluids having known fluid compositions (e.g., known fluid components and known concentrations of those fluid components). In some example implementations, the reference data in the reference database can be updated periodically or a periodically with data from formation fluid samples measured in situ, at a wellsite or other subterranean formations having similar conditions, etc. In some examples, the database may optionally be implemented with a trained neural network that represents a model of the molecular decomposition process by irradiation.

Figure 1:
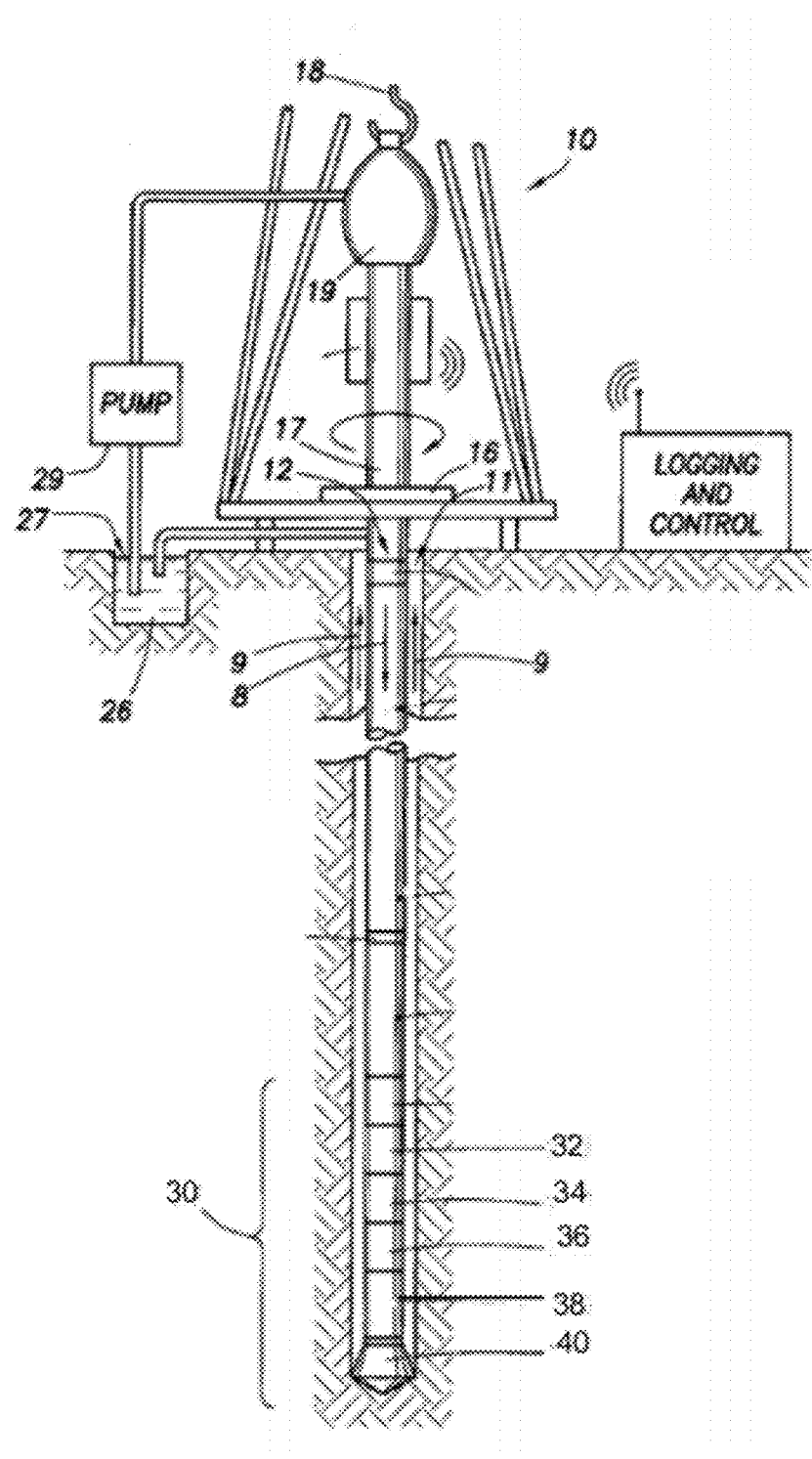
FIG. 1 depicts a wellsite system in which the example implementations described herein can be employed.

FIG. 1 illustrates a wellsite system in which the example implementations can be employed. The wellsite can be onshore or offshore. In this example system, a borehole 11 is formed in subsurface formations by rotary drilling in a manner that is well known. Some example implementations can also use directional drilling.

A drill string 12 is suspended within the borehole 11 and has a bottom hole assembly 30 that includes a drill bit 40 at its lower end. The wellsite system includes a platform and derrick assembly 10 positioned over the borehole 11. The assembly 10 includes a rotary table 16, a kelly 17, a hook 18 and a rotary swivel 19. The drill string 12 is rotated by the rotary table 16, energized by means not shown, which engages the kelly 17 at the upper end of the drill string 12. The drill string 12 is suspended from the hook 18, which is attached to a traveling block (also not shown), through the kelly 17 and the rotary swivel 19, which permits rotation of the drill string 12 relative to the hook 18. As is well known, a top drive system could alternatively be used.

In the illustrated example implementation, the wellsite system further includes drilling fluid or mud 26 stored in a pit 27 formed at the well site. A pump 29 delivers the drilling fluid 26 to the interior of the drill string 12 via a port in the rotary swivel 19, causing the drilling fluid 26 to flow downwardly through the drill string 12 as indicated by a directional arrow 8. The drilling fluid 26 exits the drill string 12 via ports in the drill bit 40, and then circulates upwardly through the annulus region between the outside of the drill string 12 and the wall of the borehole 11, as indicated by directional arrows 9. In this well-known manner, the drilling fluid 26 lubricates the drill bit 40 and carries formation cuttings to the surface as it is returned to the pit 27 for recirculation.

The bottom hole assembly 30 of the illustrated example implementation includes a logging-while-drilling (LWD) module 32, a measuring-while-drilling (MWD) module 34, a roto-steerable system and motor 38, and the drill bit 40.

The LWD module 32 is housed in a special type of drill collar, as is known in the art, and can contain one or a plurality of known types of logging tools (e.g., formation sampling tools). It will also be understood that more than one LWD and/or MWD module can be employed (e.g., as represented at 36). (References, throughout the following description, to a module at the position of 32 can alternatively mean a module at the position of 36 as well.) The LWD module 32 includes capabilities for measuring, processing, and storing information, as well as for communicating with the MWD module 34. In the illustrated example implementation, the LWD module 32 includes a sampling device (not shown).

The MWD module 34 is also housed in a special type of drill collar, as is known in the art, and can contain one or more devices for measuring characteristics of the drill string 12 and the drill bit 40. The MWD module 34 further includes an apparatus (not shown) for generating electrical power to the downhole system. This may typically include a mud turbine generator powered by the flow of the drilling fluid 26, it being understood that other power and/or battery systems may be employed. In the illustrated example implementation, the MWD module 34 includes one or more of the following types of measuring devices: a weight-on-bit measuring device, a torque measuring device, a vibration measuring device, a shock measuring device, a stick slip measuring device, a direction measuring device, and an inclination measuring device. The MWD module 34 includes capabilities for communicating with the surface equipment.

Figure 2:
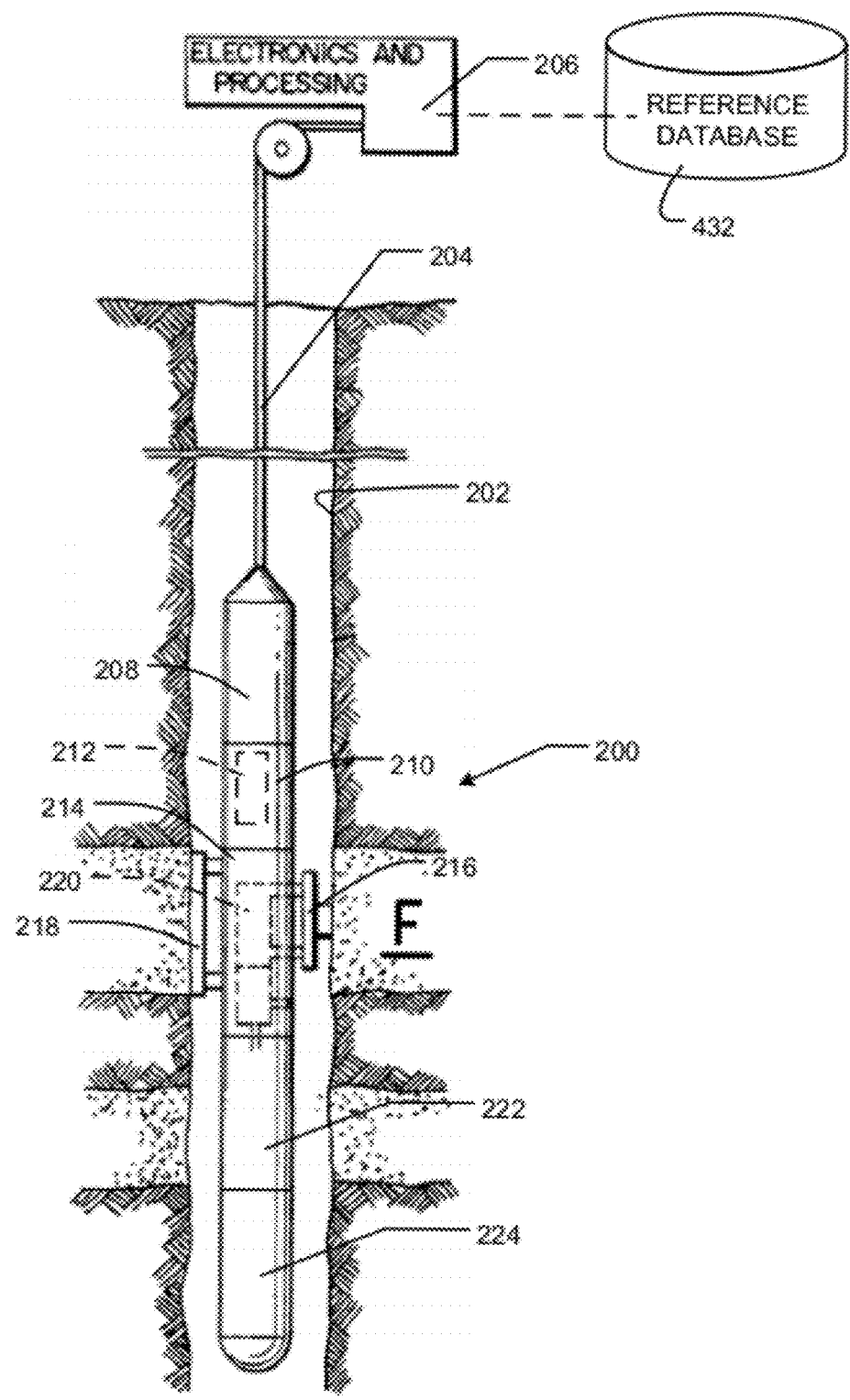
FIG. 2 depicts an example wireline tool in which the example implementations described herein can be employed.

Turning to FIG. 2, an example wireline tool 200 that may be used to extract and analyze formation fluid samples is suspended in a wellbore 202 from the lower end of a multi-conductor cable 204 that is spooled on a winch (not shown) at the Earth's surface. At the surface, the cable 204 is communicatively coupled to an electrical control and processing system 206 (which is coupled to a reference database 432 described below in connection with FIG. 5). The wireline tool 200 includes an elongated body 208 that includes a telemetry and control module 210 having a downhole control system 212 configured to control extraction of formation fluid from the formation F and measurements performed on the extracted fluid, for example, based on commands send by the electrical control and processing system 206 via the cable 204.

The wireline tool 200 also includes a formation tester module 214 having a selectively extendable fluid admitting assembly 216 and a selectively extendable tool anchoring member 218 that are respectively arranged on opposite sides of the body 208. The fluid admitting assembly 216 is configured to selectively seal off or isolate selected portions of the wall of the wellbore 202 to fluidly couple to the adjacent formation F and draw fluid samples from the formation F. The wireline tool 200 may be provided with a sampling probe 404 (FIG. 4) that is to be held against the wellbore 202. The wireline tool 200 may also be provided with a plurality of packers (not shown) that are to fill the volume between at least part of the wireline tool 200 and the wellbore 202 or any other suitable method may be used to extract a fluid sample into the wireline tool 200. The formation tester 214 also includes a fluid analysis module 220 through which the obtained fluid samples flow. The fluid may thereafter be expelled through a port (not shown) or it may be sent to one or more fluid collecting chambers 222 and 224, which may receive and retain the formation fluid for subsequent testing at the surface or a testing facility. In the illustrated example, the electrical control and processing system 206 and/or the downhole control system 212 are configured to control the fluid admitting assembly 216 to draw fluid samples from the formation F and to control the fluid analysis module 220 to measure the fluid samples. In some example implementations, the fluid analysis module 220 may be configured to analyze the measurement data of the fluid samples as described herein. In other example implementations, the fluid analysis module 220 may be configured to generate and store the measurement data and subsequently communicate the measurement data to the surface for subsequent analysis at the surface. Although the downhole control system 212 is shown as being implemented separate from the formation tester 214, in some example implementations, the downhole control system 212 may be implemented in the formation tester 214.

Figure 3:
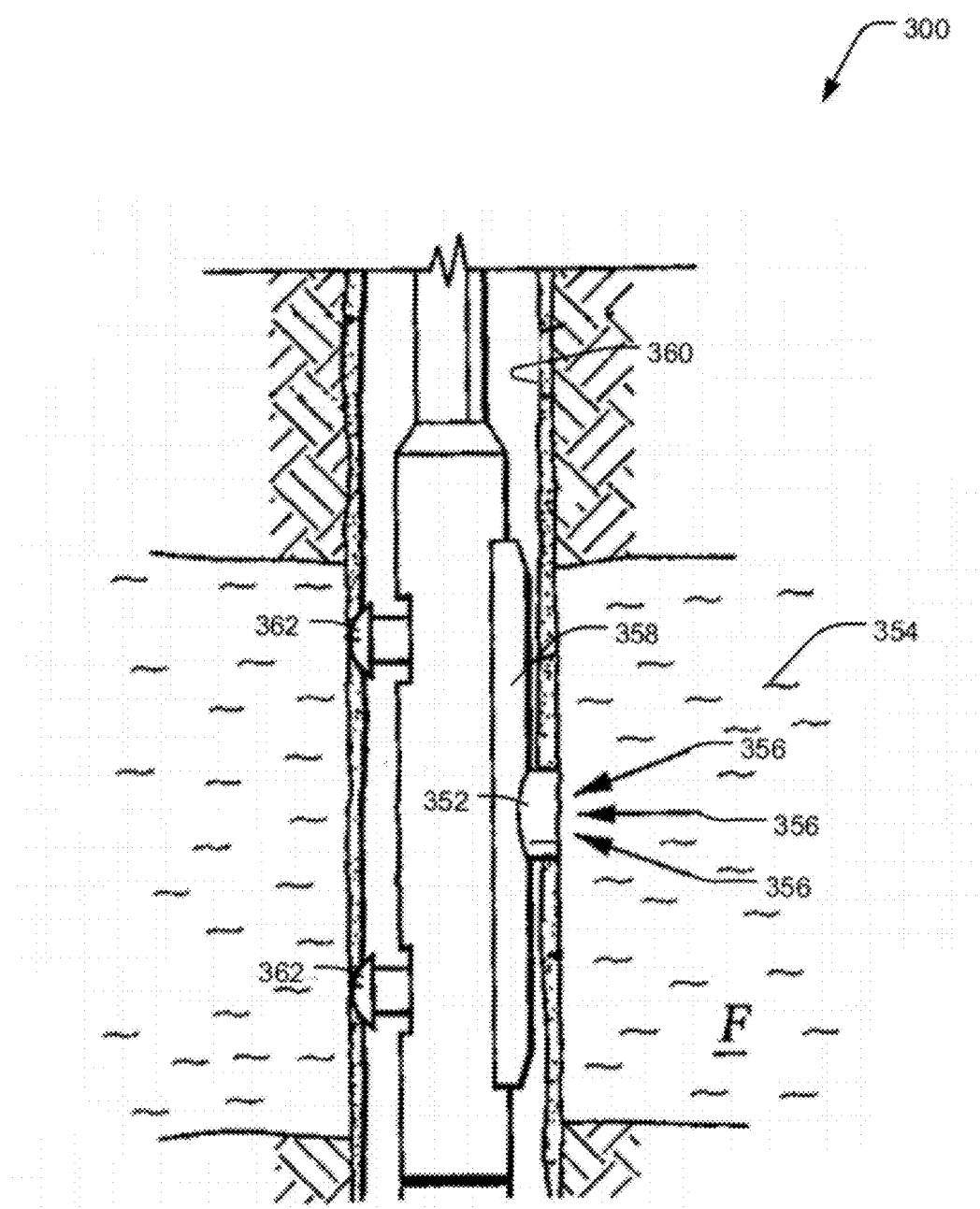
FIG. 3 depicts a simplified diagram of a logging device.

FIG. 3 is a simplified diagram of a sampling-while-drilling logging device 300 (LWD tool 300), and may be used to implement the LWD module 32 of FIG. 1. In the illustrated example, the LWD tool 300 is of a type described in U.S. Pat. No. 7,114,562, which is assigned to the assignee of the present patent and incorporated herein by reference in its entirety. However, other types of pressure measuring LWD tools can be used to implement the LWD tool 300 or part of an LWD tool. The LWD tool 300 is provided with a probe 352 for establishing fluid communication with the formation F and drawing formation fluid 354 into the LWD tool 300 in a direction generally indicated by arrows 356. The probe 352 may extend from a stabilizer blade 358 of the LWD tool 300 to engage a bore wall 360. The stabilizer blade 358 includes one or more blades that engage the bore wall 360. Once fluid is drawn into the LWD tool 300 via the probe 352, various measurements may be conducted on the sample such as, for example, a pretest parameter or a pressure parameter may be measured. The LWD tool 300 may be provided with a plurality of backup pistons 362 to assist in applying a force to push and/or move the LWD tool 300 and/or the probe 352 against the bore wall 360. Additionally, the LWD tool 300 may include sample chambers (not shown) to be used to collect fluid sample(s) for retrieval at the surface.

FIG. 4 depicts a block diagram of an example apparatus 400 that may be used to implement the example formation tester 214 of FIG. 2 and/or the LWD tool 300 of FIG. 3. In the illustrated example of FIG. 4, lines shown connecting blocks represent fluid and/or electrical connections that may comprise one or more flowlines (e.g., hydraulic fluid flowlines or formation fluid flowlines) or one or more wires or conductive paths. The apparatus 400 is preferably of modular construction.

As shown in FIG. 4, the example apparatus 400 includes a hydraulic system 402 that may be fluidly coupled to the sampling probe 404 to extend the sampling probe 404 into engagement with the formation F (FIG. 2) to enable drawing formation fluid samples via the sampling probe 404. Additionally, the hydraulic system 402 may retract the sampling probe 404 toward or into a chassis or body 406 when the sampling operation is complete. In other example implementations, the example apparatus 400 includes a plurality of packers (not shown) that are expanded toward a surface of the wellbore 202 (FIG. 2) to in-fill the volume between at least part of the wireline tool 200 (FIG. 2) and the formation F to substantially seal against the wellbore 202 (FIG. 2). In this example, to obtain a formation sample, the formation fluid flows from the formation F to a port (not shown) of the example apparatus 400.

To draw formation fluid (e.g., from the formation F), the example apparatus 400 is provided with a pump 408. In particular, the pump 408 draws formation fluid through a flowline 410, an ionizer 418, a first fluid measurement unit 420 and a second fluid measurement unit 421. In one implementation, the first and second fluid measurement units 420 and 421 may be used to determine the composition of a fluid sample and may be implemented using any suitable fluid measurement unit such as, for example, a spectrometer (an optical spectrometer or OFA, a nuclear magnetic resonance (NMR) spectrometer, a capacitance spectrometer, etc.). Specifically, the first fluid measurement unit 420 is used to measure the ionized fluid sample and the second fluid measurement unit 421 is used to measure the non-ionized fluid sample. In this example, a bypass line 416 may be optionally omitted. Although not shown, the example apparatus 400 may additionally be provided with other types of suitable sensors including, for example, a density sensor, a viscosity sensor, a flow rate sensor, etc. to measure other fluid characteristics either before or after ionization.

In an alternative example, the example apparatus 400 may not be provided with the second fluid measurement unit 421. In this example, to measure fluid samples before ionization or of non-ionized fluid samples, the example apparatus 400 is provided with the bypass line 416 that enables bypassing the ionizer 418 to allow some of the fluid samples extracted from the formation F to flow directly to the first fluid measurement unit 420 without being ionized. By selectively disabling the bypass line 416, the first fluid measurement unit 420 can be used to obtain measurements of non-ionized samples and ionized samples from the same or different locations in the formation F. The bypass line 416 may be provided with a circulating pump as described for example in U.S. Pat. Appl. Pub. No. 2006/0243033.

To ionize fluid samples, the example apparatus 400 is provided with the ionizer 418. The pump 408 draws a fluid sample into the ionizer 418, and the ionizer 418 ionizes the sample by exposing the sample to, for example, lightwaves, an ionizing radiation, etc. for a predetermined duration at a predetermined energy level to, for example, cause a molecular decomposition process to provide an ionized or decomposed fluid sample that can be measured using the first fluid measurement unit 420. The ionizing duration is the amount of time for which a formation fluid sample is to be exposed to an ionizing radiation source, and the energy level is an energy level sufficiently high enough to cause the fluid sample to be sufficiently ionized to obtain fluid measurement values that can be used to determine its fluid composition. The energy level may be an energy level of ultraviolet (UV), extreme ultraviolet, near ultraviolet, and/or near infrared (NIR) radiation that is required to break molecular carbon-carbon bonds and/or break the larger hydrocarbon chains into smaller hydrocarbon chains such as methane C1, ethane C2, propane C3, butane C4 or pentane C5, of fluid samples. In some examples, irradiation may change a bonding structure as well as break down the molecules within the sample. Thus, the change in bonding structure from molecules can result in a change in their color or equivalently a change in their electronic spectrum.

To identify and/or detect the presence and concentration of a plurality of analytes, species and/or molecules in fluid samples, the fluid measurement units 420 and 421 can be provided with a plurality of optical spectrometer channels or spectrometers configured to measure an optical absorption of a fluid at a plurality of wavelengths corresponding to small hydrocarbon molecules present in those analytes, species and/or molecules of interest. Thus, if the fluid measurement units 420 and 421 are to measure spectroscopic characteristics of fluid samples, the fluid measurement units 420 and 421 can be implemented using one or more spectrometers configured to measure an optical absorption (e.g. an optical density OD) at a single wavelength (e.g., a wavelength parameter) or at a plurality of wavelengths (e.g., a plurality of wavelength parameters). For example, the optical absorption values obtained in the near infra read (NIR) range from the measurement units 420 and/or 421 may, for example, be used to determine values of one or more of C1, C2, C3-5, and C6+ concentrations or relative fractions of non-ionized fluid sample and ionized fluid samples, as well as other non-hydrocarbon concentrations or relatives fractions, such as $CO_2$, $H_2O$. In this manner, subsequent comparative analyses between the non-ionized sample measurements and ionized sample measurements can be used to detect changes in particular components (e.g., increases in levels of C1-C5 and decreases in C6+) attributed to the breaking of chemical bonds (e.g., heavy hydrocarbons). In other examples, the fluid measurement units 420 and/or 421 can measure the fluid coloration of non-ionized fluid sample and ionized fluid samples. Color absorption is mainly caused by electron excitation in aromatic molecules (such as asphaltene), which covers the wavelength range of visible to near infrared spectroscopy. The fraction of the fluid sample that is colored may be the fraction of the fluid sample that is absorbing, for example, lightwaves emitted by the ionizer 418. Specifically, first and second fluid measurement units 420 and 421 respectively may measure the change in the coloration of the sample to determine the chemical alteration of the colored fraction of the fluid sample. The change of fluid coloration may in turn be related to asphaltene concentration in the sample. In yet other examples, the fluid measurement units 420 and 421 may measure fluorescence properties of the fluid sample. Specifically, first and second fluid measurement units 420 and 421 respectively may measure the change in the fluorescence of the sample to determine the chemical alteration of the aromatic fraction of the fluid sample. Additionally or alternatively other fluid properties such as viscosity may also exhibit change after ionization and may advantageously be measured by the fluid measurements unit 420 and 421. In any case, the parameter measurement values obtained using the fluid measurement units 420 and 421 may be used to identify particular analytes, species, atoms and/or molecules present in fluid samples based on models of molecular decomposition processes for those analytes, species, atoms or molecules caused by the ionization process of the ionizer 418.

To store or discard formation fluid samples, the pump 408 moves the fluid away from the first fluid measurement unit 420 to a valve 422, which has a first selectable outlet 424 that is fluidly coupled to a fluid store 426 and a second selectable outlet 428 that expels fluid out of the apparatus 400 into, for example, a wellbore.

To control the hydraulic system 402, the pump 408, the ionizer 418, the first and second fluid measurement units 420 and 421, and the valve 422, the example apparatus 400 is provided with the downhole control and data acquisition system 430. Although not shown, the downhole control and data acquisition system 430 may include a processor, one or more memories, and a communication interface (e.g., a modem). The communication interface of the downhole control and data acquisition system 430 may be communicatively coupled to a surface system (e.g., the electrical control and processing system 206 of FIG. 2) via wires or lines 434 and/or the cable 204 (FIG. 2) to communicate analysis data and/or receive control data. The wires or lines 434 may include a databus (e.g., for carrying digital information and/or analog information), electrical power lines, etc. and may be implemented using a single conductor or multiple conductors.

In operation, the downhole control and data acquisition system 430 may be used to control the hydraulic system 402 to extend the sampling probe 404 to engage the formation F. The downhole control and data acquisition system 430 may also control the pump 408 to draw formation fluid through the flowline 410, the ionizer 418, and the first fluid measurement unit 420. In addition, the downhole control and data acquisition system 430 can be used to enable and disable the bypass line 416.

To store reference measurement values of reference formation fluids known to include particular species and/or to have particular fluid compositions for use in subsequently determining fluid compositions of formation fluid samples, the downhole control and data acquisition system 430 may store or be communicatively coupled to the reference database 432 (FIG. 5). In some example implementations, the reference database 432 may be additionally or alternatively stored in the electrical control and processing system 206 of FIG. 2. An example implementation of the reference database 432 is depicted in FIG. 5.

In other examples, the example apparatus 400 may be provided with one or more chamber(s) or tank(s) 436 to hold a diluent, a UV transparent solvent that is to be mixed with and/or exposed to a formation fluid sample to reduce the effective density of the sample before the sample enters the fluid measurement units 420 and 421 and/or the ionizer 418. The mixing of the formation fluid sample and the solvent conveyed in one of the tanks 436 may be facilitated by implementing an inline mixer (not shown) on the flow line 410. Alternatively or additionally, the one or more chamber(s) or tank(s) 436 may hold any other suitable substance, such as oxygen or air, to be mixed with the formation fluid sample. For example, air may be added to facilitate oxidation of large hydrocarbons chains contained in the fluid sample to generate carbon dioxide and other substances, as explained in further details in the description of FIG. 11.

Turning to FIG. 5, the example reference database 432 may be configured or structured to store data generated using any suitable fluid analysis technique including the fluid analysis techniques described herein. In some example implementations, the reference measurement data stored in the reference database 432 may be generated using laboratory or uphole fluid analyses of fluid samples known to have particular fluid compositions (e.g., fluid samples known to have particular atoms and/or molecules and known concentrations of those atoms and/or molecules).

In the illustrated example of FIG. 5, the reference database 432 includes an atom/molecule identifier column 502, a plurality of reference parameter measurement values columns 504, an ionization energy exposure duration column 506, and an ionization energy level column 508. The atom/molecule identifier column 502 may be used to store names or identifiers of reference fluids known to have particular components (e.g., particular species, atoms or molecules) that may be found in formation fluid samples. The reference parameter measurement values columns 504 are used to store reference measurement values of reference fluids, concentrations of those components and/or fractions (e.g. weight fractions, molar fractions) of those components. As described above, the reference measurement values stored in the reference parameter measurement values columns 504 may be measured in a laboratory environment or some other uphole environment under controlled conditions using any suitable fluid analysis technique including the fluid analysis techniques described herein. In the illustrated example, the reference parameter measurement values columns 504 include a non-ionized sample column 510 to store measured parameter values of reference fluid samples prior to ionization, an ionized sample column 514 to store measured parameter values of reference fluid samples after or during ionization, and a relationship column 516 to store for example ratios, differences, or correlations values indicative of changes between the reference measurement values for the non-ionized samples and the reference measurement values for the ionized samples (e.g., non-ionized-to-ionized relationships). In other words, the reference database may describe how the values of measurements performed by the fluid measurements units 420 and/or 421 and relative to known reference fluids are affected by the ionizer 418 or the like, as a function of, for example, the light intensity and exposure time. Thus, the reference database 432 may provide a model or description of the molecular decomposition process and/or of the bonding structure change by an ionizer (e.g. the ionizer 418 of FIG. 4).

The ionization energy exposure duration column 506 is used to store the duration or amount of time for which each reference fluid sample is ionized (e.g., exposed to an ionization source). The ionization energy level column 508 is used to store energy levels used to ionize the reference fluid samples. If an ionization technique involves emitting a light-wave source (e.g., an ultraviolet light source) onto a fluid sample, the exposure duration selected and the energy level stored in the columns 506 and 508, respectively, may be selected based on the amount of energy and the duration of exposure to that energy that is needed to induce particle breakdown of larger molecular mass (or molar mass) hydrocarbons into smaller hydrocarbon chains.

Figure 6:
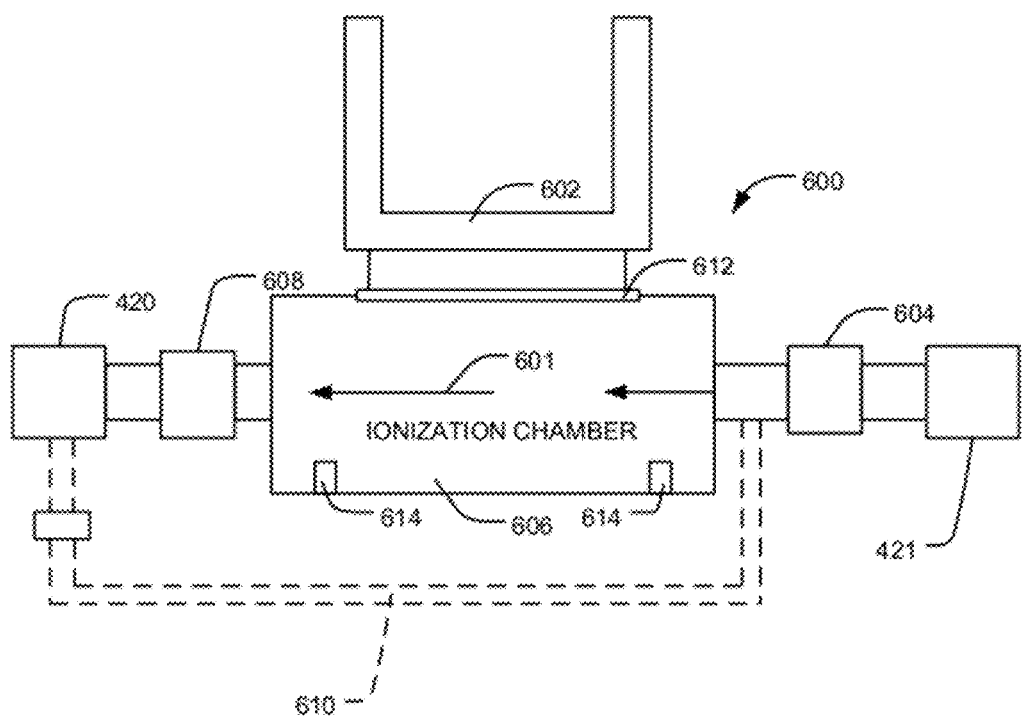
FIG. 6 depicts a block diagram of an example ionizer that may be used to implement the example apparatus of FIG. 4.

Now turning to FIG. 6, a detailed block diagram is shown of an example ionizer 600, which may be used to implement the ionizer 418 of FIG. 4. In the illustrated example, the ionizer 600 is configured to ionize formation fluid samples by exposing the fluid samples to an ionizing source 602 that emits light waves at a particular wavelength. The ionizing source 602 may be any suitable source such as, for example, a lightwave emission source (e.g., UV light at a wavelength of approximately 254 nm or any other suitable wavelength in the visible to infrared range capable of absorption by carbon-carbon bonds and/or by most molecules that are aromatic in nature such as substituted benzenes, non-substituted benzenes, napthalenes, phenanthrenes, etc.), etc. In the illustrated example, the ionizer 600 includes a fluid inlet 604, an ionization chamber 606, a fluid outlet 608, a fluid bypass line 610, and a window 612 (e.g., a UV transparent window, a window comprising a quartz material or any other suitable window) that is mounted or coupled to the ionization chamber 606 in a structural configuration that substantially maintains a pressure within the ionization chamber 606 and/or prevents substantial change in the pressure within the ionization chamber 606. The bypass line 610 may allow for the fluid sample to bypass the ionization chamber 606. For example, if the ionization techniques described herein are not to be used to analyze a particular sample or a particular number of samples, the example apparatus 400 of FIG. 4 may be configured to use the bypass line 610 to enable the fluid samples to bypass the ionization chamber 606. In this manner, the one or more fluid samples can be analyzed by the first fluid measurement unit 420 and/or be stored in the fluid store 426 (FIG. 4) or be expelled into the wellbore 202 (FIG. 2). However, in some examples, the example ionizer 600 may be provided with the second fluid measurement unit 421 and, thus, the bypass line 610 may be omitted.

To ionize a fluid sample, as the fluid sample flows into the ionization chamber 606 via the fluid inlet 604 in a direction generally indicated by arrow 601, the ionizing source 602 (e.g., a UV tube) emits an ionizing energy through the window 612 onto the fluid sample in the ionization chamber 606 and the energy is absorbed by the fluid sample. The fluid sample may be moved through the ionization chamber 606 at any suitable speed. In some instances, the fluid sample may be moved at a relatively slow speed to increase the exposure duration of the fluid sample to the ionizing source 602. Thus, because inducing particle breakdown of higher molecular mass (or molar mass) hydrocarbons into lower molecular mass (or molar mass) hydrocarbons varies as a function of time, the fluid sample speed may be controlled to achieve different amounts of ionization and potential molecular breakdown. By not exposing the ionizing source 602 to the pressure within the ionization chamber 606, the ionizing source 602 can be constructed using materials that do not have to withstand being exposed to the pressure within the ionization chamber 606 (e.g., formation pressure) and/or being exposed to the fluid sample. In some example implementations, the ionization chamber 606 is constructed from a substantially UV transparent material (e.g., a light filtering material that allows transmission therethrough of UV light) and the ionizing source 602 may be at least partially wrapped around the ionization chamber 606 (e.g., in a configuration substantially similar or identical as an example ionizer 800 described below in connection with FIG. 8).

The ionizing source 602 is implemented using a lightwave source such as, for example, a UV lightwave source. The absorbed lightwave ionizing energy may decomposes molecules (e.g., hydrocarbon molecules) in the fluid sample having relatively higher molecular mass (or molar mass) (e.g., relatively longer hydrocarbon chains) into molecules having relatively lower molecular mass (or molar mass) (e.g., relatively shorter hydrocarbon chains having a molecular mass (or molar mass) less than $C_6H_{14}$). However, in some cases the ionizing energy may also increase the molar mass of the formed molecules or the molar mass may remain constant and a different isomer may be formed. When the ionized fluid sample exits the ionization chamber 606 via the fluid outlet 608, a parameter (e.g., an optical density parameter) of the ionized sample can be measured using, for example, a spectrometer, a chromatographer, etc. of the first fluid measurement unit 420 to quantify the types and concentrations of the relatively smaller molecular mass (or molar mass) molecules in the ionized fluid sample. In this manner, the spectroscopic parameter measurement values of a non-ionized sample and the spectroscopic parameter measurement values of the sample after ionization can be compared to reference data stored in a database (e.g., the database 432 of FIG. 5) to identify species and/or analyte(s) in the fluid sample and/or to determine a fluid composition and fluid component concentrations of the fluid sample. While a database may be used, other interpretations techniques using the spectroscopic parameter measurement values of the sample after ionization and the spectroscopic parameter measurement values of a non-ionized sample may be used to identify species and/or analyte(s) in the fluid sample and/or to determine a fluid composition and fluid component concentrations of the fluid sample.

Although the first fluid measurement unit 420 is shown in FIG. 6 as placed in a serial configuration with the ionization chamber 606, in other example implementations, the first fluid measurement unit 420 can be located in or relatively closer to (e.g., in engagement with or within) the ionization chamber 606 to enable measuring ionized fluid samples while they are exposed to ionizing sources. For example, in some instances a fluid sample may remain in an ionized state for a relatively short duration, and it may facilitate measuring the ionized fluid by locating the first fluid measurement unit 420 closer to or in the ionization chamber 606.

Figure 7:
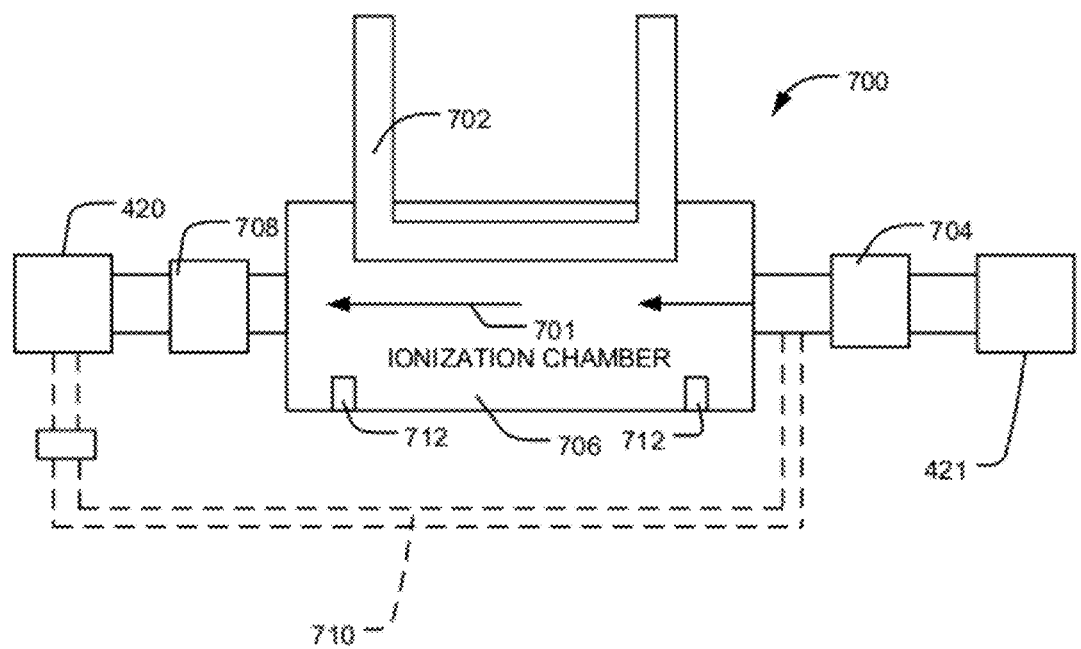
FIG. 7 depicts another block diagram of another example ionizer that may be used to implement the example apparatus of FIG. 4.

FIG. 7 is a detailed block diagram of another example ionizer 700, which may be used to implement the ionizer 418 of FIG. 4. In the illustrated example, the ionizer 700 includes an ionizing source 702, a fluid inlet 704, an ionization chamber 706, a fluid outlet 708, and a fluid bypass line 710. In the illustrated example, the ionizing source 702 is at least partially in the ionization chamber 706 and is configured to ionize formation fluid samples by exposing the fluid samples to the ionizing source 702 that emits light waves. The ionizing source 702 may be any suitable source such as, for example, a lightwave emission source. The ionizing source 702 may be configured in a pipe-like shape and may be housed in or contained in a UV, an opaque material, a sapphire material or any other suitable material that allows transmission of UV energy and/or radiation into a fluid sample. In addition, the ionizing source 702 is constructed to withstand pressures (e.g., formation pressure) to which it is exposed by being at least partially located in the ionization chamber 706 and exposed directly to fluid samples. Positioning the ionizing source 702 at least partially within the ionization chamber 706 increases the amount of exposure that the fluid sample has to the ionizing source 702 (e.g., by causing the fluid sample to surround the circumference of the ionizing source 702). In other example implementations, the ionizing source 702 may be any other suitable size and/or shape that may increase the surface area exposure of the fluid sample to the ionizing source 702 such as, for example, coiling the ionizing source 702 within the ionization chamber 706.

In the illustrated example, the bypass line 710 enables the fluid sample to bypass the ionization chamber 706. For example, if the ionization techniques described herein are not to be used to analyze a particular sample or a particular number of samples, the example apparatus 400 of FIG. 4 may be configured to use the bypass line 710 to enable the fluid samples to bypass the ionization chamber 706, to be analyzed by the first fluid measurement unit 420, and/or to be stored in the fluid store 426 (FIG. 4) or be expelled into the wellbore 202 (FIG. 2). However, in some examples, the example ionizer 700 may be provided with the second fluid measurement unit 421 and, thus, the bypass line 710 may be omitted.

To ionize a fluid sample, as the fluid sample flows into the ionization chamber 706 via the fluid inlet 704 in a direction generally indicated by arrow 701, the ionizing source 702 emits an ionizing energy onto the fluid sample in the ionization chamber 706 and the energy is absorbed by the fluid sample. The fluid sample may be moved through the ionization chamber 706 at any suitable speed, which may be increased or decreased to change the amount of exposure of the fluid sample to the ionizing source 702 and to induce different amounts of particle breakdown. In some examples, the ionization chamber 706 is constructed using a material (e.g., a metal) to facilitate or enable maintaining a substantially stable pressure of a fluid as the fluid is moved within the ionization chamber 706.

In some examples, the example ionizers 600 or 700 may be provided with electrodes 614 (FIG. 6) and 712 (FIG. 7) that are disposed within the ionizing chamber 706 to apply an electrical field in addition to UV ionization, for example to move anions and cations created during the ionization of the fluid sample away. Specifically, this technique may be used to improve molecular breakdown and/or diminish the reformation of ionized molecules.

Figure 8:
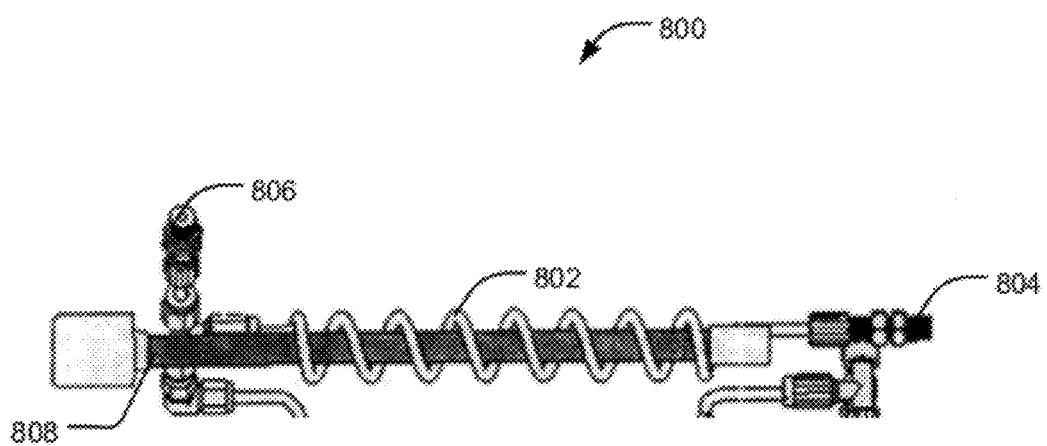
FIG. 8 depicts an example ionizer structure that may be used to implement the example ionizer of FIGS. 6 and 7.

FIG. 8 depicts a top view of the example ionizer 800 that may be used to ionize a fluid sample in a laboratory setting and/or may be modified to be used in a downhole environment. In the illustrated example, the ionizer 800 includes a flowline 802 having a fluid inlet 804 and a fluid outlet 806 to enable formation fluid to flow through the flowline 802. As shown in FIG. 8, the flowline 802 is wrapped, spiraled or coiled around an ionizing radiation source 808, which may be implemented using any suitable ionization radiation source including, for example, a hot cathode mercury filled lamp. As fluid samples are drawn through the flowline 802, the samples absorb energy (e.g., radiation energy, etc.) emitted by the ionizing radiation source 808 to, for example, induce particle breakdown of relatively higher molecular mass (or molar mass) hydrocarbons in the samples into relatively lower molecular mass (or molar mass) hydrocarbons. The spiraled or coiled configuration of the flowline 802 ensures that substantially the entire formation fluid of each sample is exposed to the ionizing radiation source 808. In other example implementations, the flowline 802 may be arranged in any other suitable configuration that will increase the surface area exposure of the fluid sample to the ionizing radiation source 808 through, for example, laminar and/or turbulent flow.

To enable light energy from the ionizing radiation source 808 to reach the formation fluid samples in the flowline 802, the flowline 802 may be implemented using a transparent or semi-transparent material such as, for example, a polytetraethylene (PTE) material, a polytetrafluoroethylene (PTFE) material, etc. However, other semi-transparent materials and/or other suitable materials may be implemented that are more resilient to downhole pressures. In addition, to facilitate the formation fluid samples to absorb all or substantially all of the ionizing energy emitted by the ionizing radiation source 808, the flowline 802 may be implemented to include optically reflective inner surfaces to, for example, reflect light energy within the flowline 802 through the formation fluid sample and/or to trap light energy emitted by the ionizing radiation source 808 in the flowline 802 until the formation fluid sample absorbs all or substantially all of the light energy. Though one flowline is shown in the illustrated example, any number of flowlines (e.g., 2, 3, 4, 5, etc.) may be included instead. Further, though one ionizing radiation source is shown in the illustrated example, any number of ionizing radiation sources (e.g., 2, 3, 4, 5, etc.) may be used instead. In some example implementations, a photo-catalyst such as, for example, titanium dioxide ($TiO_2$), which may be used in an anatase form, may be added to the formation fluid sample prior to ionizing the sample. Titanium dioxide becomes a photo-catalyst when exposed to ultraviolet light and facilitates the acceleration of ionizing the sample.

Figure 9:
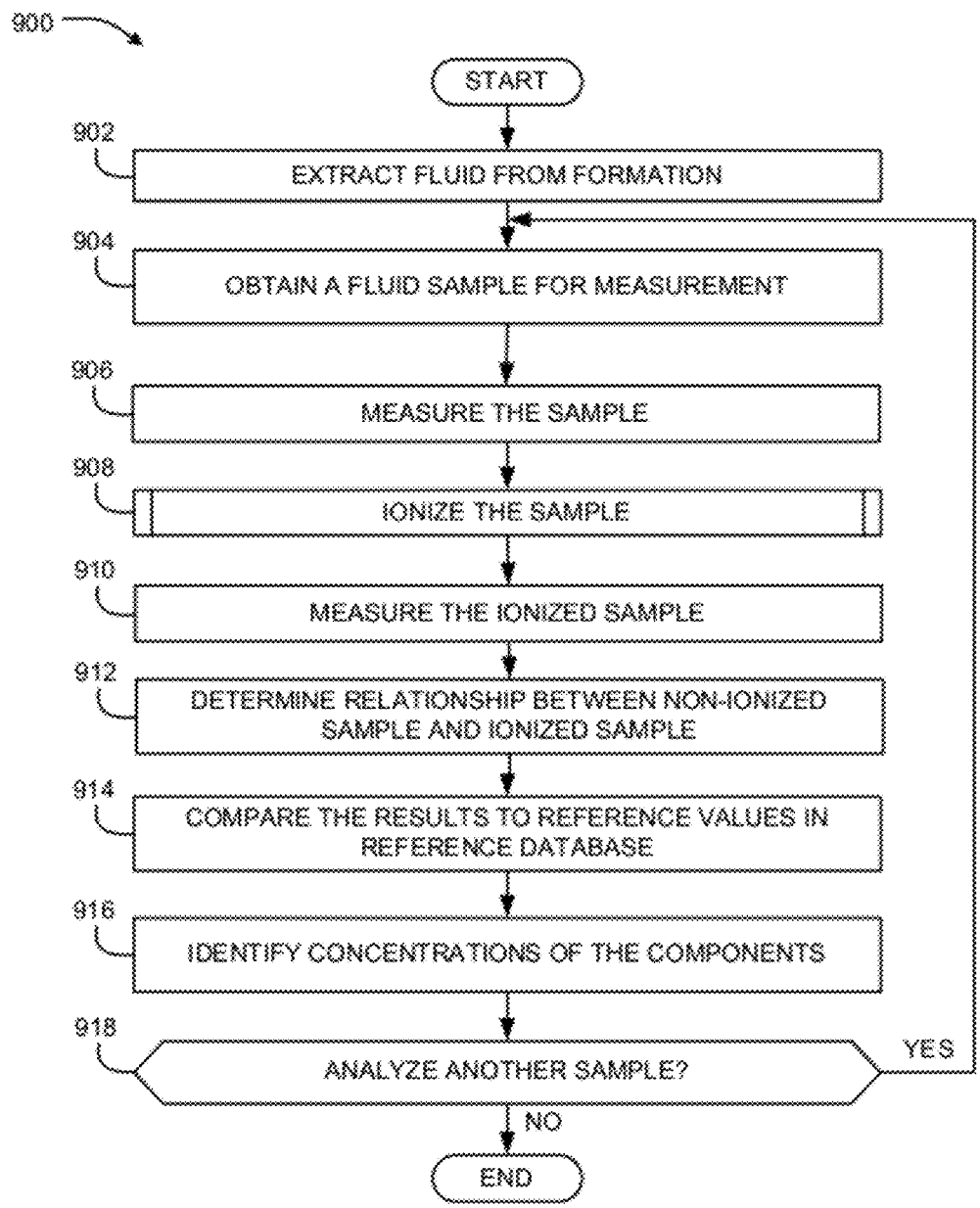
FIG. 9 is a flow diagram of an example method that may be used to identify fluid components and component concentrations in formation fluid samples.
Figure 10:
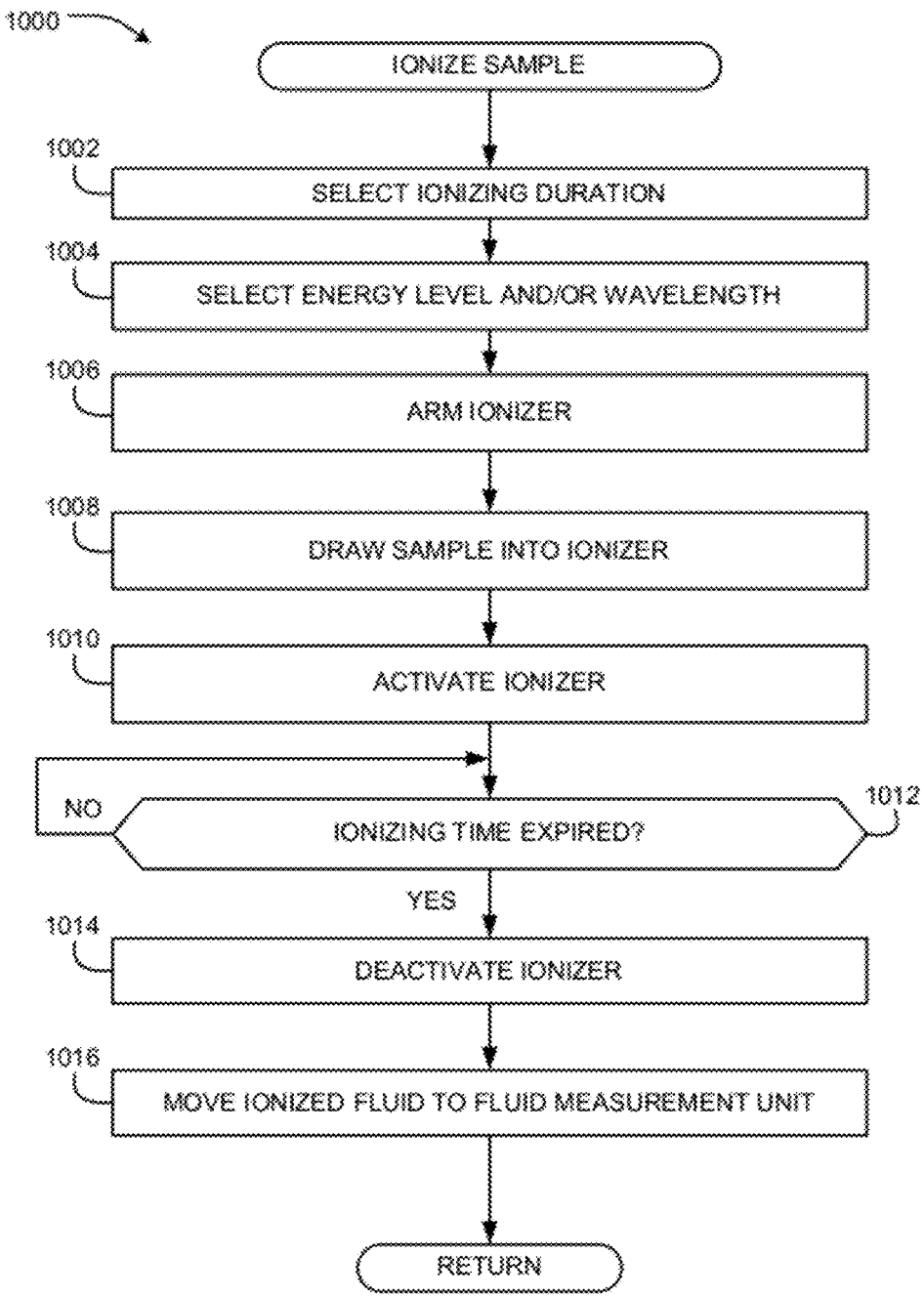
FIG. 10 is a flow diagram of an example method that may be used to perform measurements of formation fluid samples.

FIGS. 9 and 10 are flowcharts of example methods that can be used to draw and analyze formation fluid samples from a subterranean formation (e.g., the formation F of FIG. 2). The example methods of FIGS. 9 and 10 may be used to implement the example formation tester 214 of FIG. 2, the example apparatus 400 of FIG. 4, and/or the example ionizers 600, 700, and 800 of FIGS. 6, 7 and/or 8. The example methods of FIGS. 9 and 10 may be implemented using software and/or hardware. In some example implementations, the flowcharts can be representative of machine readable instructions and the example methods of the flowcharts may be implemented entirely or in part by executing the machine readable instructions. Such machine readable instructions may be executed by one or both of the electrical control and processing system 206 (FIG. 2) and/or the downhole control and data acquisition system 430 (FIG. 4). In particular, a processor or any other suitable device to execute machine readable instructions may retrieve such instructions from a memory device (e.g., a random access memory (RAM), a read only memory (ROM), etc.) and execute those instructions. In some examples, one or more of the operations depicted in the flowcharts of FIGS. 9 and 10 may be implemented manually. Although the example methods are described with reference to the flowcharts of FIGS. 9 and 10, persons of ordinary skill in the art will readily appreciate that other methods to implement the formation tester 214, the example apparatus 400, and/or the example ionizers 600, 700, and 800 to analyze formation fluid samples may additionally or alternatively be used. For example, the order of execution of the blocks depicted in the flowcharts of FIGS. 9 and 10 may be changed and/or some of the blocks described may be rearranged, eliminated, or combined.

Turning now to FIG. 9, the illustrated flow diagram depicts an example method 900 that may be used to draw and analyze formation fluid samples using, for example, the example apparatus 400 of FIG. 4. Initially, the sampling probe 404 (FIG. 4) extracts (e.g., admits, draws, etc.) fluid from the formation F (block 902). The first fluid measurement unit 420 (FIG. 4) obtains a formation fluid sample for measurement (block 904). The first fluid measurement unit 420 then measures a portion of the non-ionized fluid sample obtained via the bypass line 416 (block 906). However, the example apparatus 400 may be provided with the second fluid measurement unit 421 (FIG. 4) that is positioned before the ionizer 418 (FIG. 4) and adjacent the sampling probe 404 (FIG. 4), which obtains a formation fluid sample for measurement and then measures a portion of the non-ionized fluid sample. For example, the first and second fluid measurement units 420 and 421 may use a downhole fluid analysis (DFA) technique (e.g., spectroscopy measurements such as Optical Densities, downhole density/viscosity measurements etc.) as discussed above to collect values that can be used to determine or identify species and/or analyte(s) in the fluid sample and/or fluid components and concentrations of those components in the fluid sample.

The ionizer 418 ionizes a fluid sample (block 908) by, for example, exposing the sample to a UV energy, an ionizing radiation, etc. for a particular amount of time at a particular energy level. The duration of exposure and the energy level to be used may be determined or selected based on experiments with similar samples to determine the amount of exposure and the energy level that may be needed to ionize the sample to, for example, generate small enough hydrocarbon chains that can be detected by the first fluid measurement unit 420. The example method discussed below in connection with FIG. 10 may be used to implement the operation of block 908 to ionize the fluid sample. The first fluid measurement unit 420 then measures the ionized fluid sample (block 910). The downhole control and data acquisition system 430 (FIG. 4) and/or the electrical control and processing system 206 may be configured to store the measurement data corresponding to the non-ionized sample and the ionized sample in a memory (e.g., a database). The non-ionized sample and the ionized sample are to be obtained from the same or substantially the same formation fluid extracted from the formation F.

In real time or during a post process, the downhole control and data acquisition system 430 can determine a relationship between the non-ionized sample and the ionized sample (block 912) based on the measurement values. The downhole control and data acquisition system 430 may then compare the measurement values and/or identified relationships between the non-ionized and the ionized fluid samples to the reference measurements (of known fluid compositions) stored in the reference database 432 (block 914). For example, the reference database 432 can associate the presence and or the concentration of higher molecular mass (or molar mass) hydrocarbons in the non-ionized sample with reference measurement values (e.g., spectroscopic parameter values, optical density values) performed on the ionized and optionally non-ionized reference fluids. Thus, the downhole control and data acquisition system 430 may identify the concentrations of the fluid component(s) (or ranges and types of components) in the downhole fluid sample (block 916) based on agreement or similarities between the measurement values and/or relationships obtained with the non-ionized and the ionized downhole fluid samples and the reference values in the reference database 432 corresponding to one reference fluid or a mixture of reference fluids.

An example manner that may be used to identify species and/or analyte(s) in the fluid sample and/or to determine the fluid composition of the fluid sample involves comparing the measured parameter values for the fluid sample before and after ionization as a function of ionization energy exposure time to reference parameter values in the reference database 432. In another example, as shown in FIG. 5, ionization energy exposure times in the ionization energy exposure duration column 506 are stored in association with respective ones of reference relationship values stored in the ratio column 516. If the relationship value determined from the measured parameter values corresponding to the formation fluid sample matches a particular one of the relationship values of the reference measurements in the reference database 432, the downhole control and data acquisition system 430 can determine that the measured formation fluid sample includes a species, molecule or atom stored in the reference database 432. Further, the downhole control and data acquisition system 430 can determine the concentration of the species, molecule or atom based on, for example, the ionization energy level and exposure duration.

The downhole control and data acquisition system 430 then determines whether it should analyze another formation fluid sample (block 918). For example, if the example apparatus 400 has drawn another formation fluid sample and the downhole control and data acquisition system 430 has not received an instruction or command to stop analyzing fluid, the downhole control and data acquisition system 430 may determine that it should analyze another fluid sample (block 918). Otherwise, the example process of FIG. 9 is ended.

FIG. 10 is a flow diagram depicting an example method 1000 that may be used to implement the fluid ionization operation of block 908 of FIG. 9. Initially, the downhole control and data acquisition system 430 selects an ionization duration (block 1002). The ionization duration is the amount of time for which the formation fluid sample is to be exposed to, for example, the ionizing source 602 (FIG. 6), or 702 (FIG. 7) or the ionizing radiation source 808 of FIG. 8. The downhole control and data acquisition system 430 selects an energy level and/or wavelength to use for the ionizing source (block 1004). For example, the energy level and/or wavelength may be selected to control how or how much the ionizing source 602, or 702 or the ionizing radiation source 808 ionizes the fluid sample. In some example implementations, the ionizing duration and/or the energy level and/or wavelength may be preselected (e.g., prior to lowering the wireline tool 200 into the wellbore 202 of FIG. 2, at an assembly time of the formation tester 214, etc.). For example, the chemical composition (e.g., mercury) used to fill vacuum tubes to implement the ionizing radiation source 808 may dictate the wavelength available for ionizing.

After the time and the energy level are selected, the downhole control and data acquisition system 430 arms the ionizer 418 (block 1006). Arming the ionizer 418 initiates a preparation phase of the ionizer 418 to be able to ionize a fluid sample. For example, during a preparation phase, the ionization sources may be charged or energized. A fluid sample is drawn into the ionizer (block 1008), and the downhole control and data acquisition system 430 activates the ionizer 418 (block 1010). The ionizer 418 may ionize the fluid sample using any suitable ionizing technique including, for example, exposing the fluid sample to an ionizing light source as described in connection with FIGS. 6, 7, and 8. To ensure that the ionizer 418 ionizes the fluid sample for the duration selected at block 1002, the downhole control and data acquisition system 430 checks to determine if the selected amount of time has expired (block 1012) using, for example, a timer or counter. Control remains at block 1012 until the downhole control and data acquisition system 430 determines that the selected amount of time has expired. When the time expires, the downhole control and data acquisition system 430 deactivates the ionizer 418 (block 1014). The ionized fluid sample is then moved to the first fluid measurement unit 420 (block 1016). Control then returns to a fluid analysis process such as, for example, the process of FIG. 9.

Figure 11:
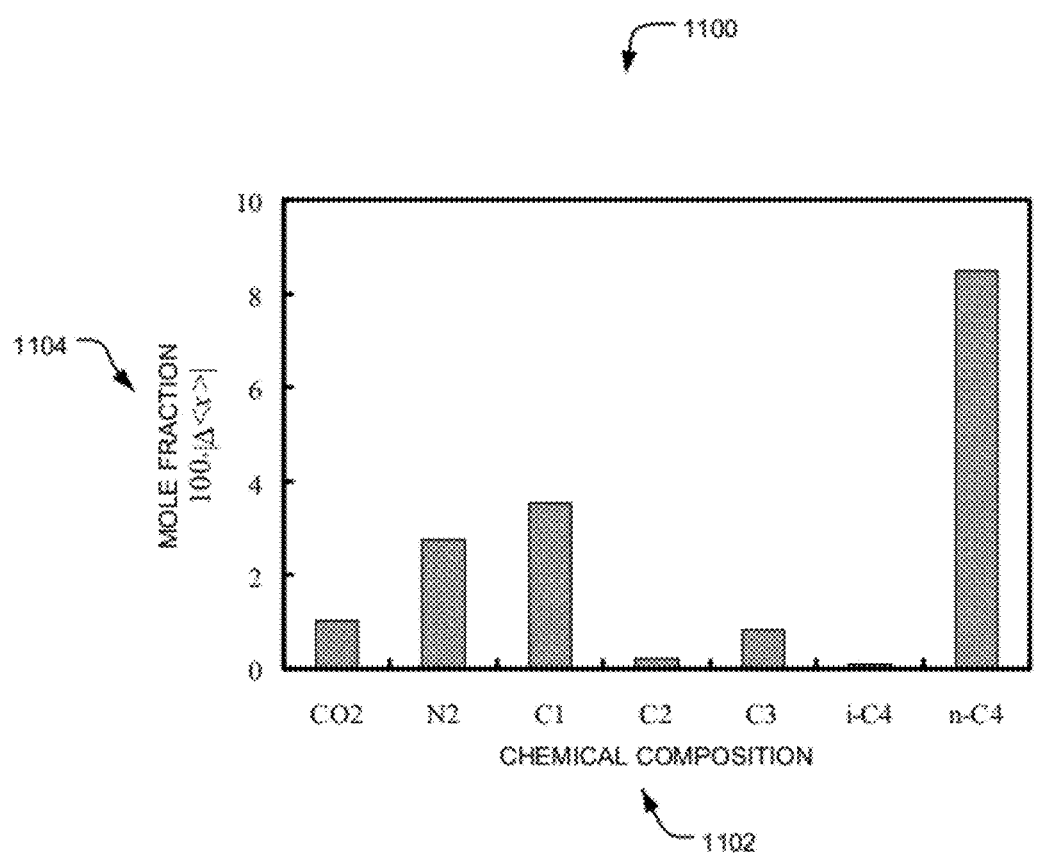
FIG. 11 is a graph that depicts the results of a fluid analysis process.

FIG. 11 depicts a graph 1100 that shows the results of a fluid analysis process in which a fluid sample (e.g., n-C4) was exposed to UV radiation (e.g., 256 nm) twice for a period of two hours. For each radiation exposure, a chemical composition 1102 of the fluid sample was determined before and after the exposure to the UV radiation. A molar fraction difference between the chemical composition before UV radiation exposure and the chemical composition after UV radiation exposure, $\Delta x$ (e.g., $\Delta x = x(a) - x(b)$), was determined for each of the two successive ionization processes. The normalized mean absolute value of the differences $100|\Delta<x>|$ 1104 is represented as a function of the different species (e.g., the different components of the ionization sample).

The graph 1100 shows differences of mole fractions in amounts of the illustrated components ($CO_2$, $N_2$, C1, C2, C3, i-C4, n-C4) between a non-ionized state and an ionized state of the fluid sample. For clarity, the mole fraction for n-C4 has been truncated and is actually over 90%. In the illustrated example, the measured amounts of the different components can be used to compare to reference measurement values stored in the reference parameter measurements values columns 504. If the measured amounts of the different components are associated with (e.g., substantially similar to) the reference parameter measurement values, the atoms and/or molecules in the formation fluid samples prior to and/or after ionization may be identified and stored in the atom/molecule identifier column 502. For example, reference parameter measurements values columns 504 may be indicative of the presence of n-C4 in a formation fluid sample. This illustrative example may thus allow distinguishing between C3, n-C4, i-C4, or C5 in a formation fluid sample for example based on amount of methane, ethane and/or carbon dioxide formed by the ionization process and measured by a near infra red optical spectrometer.

Note that the presence of nitrogen ($N_2$) in the chemical composition may be from air that was contained within the wireline tool 200 or within the ionization chamber 606. Note also that if the nitrogen was present in the wireline tool 200 or within the ionization chamber 606, the mole fraction of carbon dioxide ($CO_2$) is roughly 2% below the mole fraction of nitrogen. Thus, the measured ratio of nitrogen to carbon dioxide ($N_2/CO_2$) is about 3, which may indicate that the carbon dioxide is not solely from air contained within the wireline tool 200. The presence of the carbon dioxide may be a result of carbon dioxide formed by radical reactions during ionization.

Figure 12:
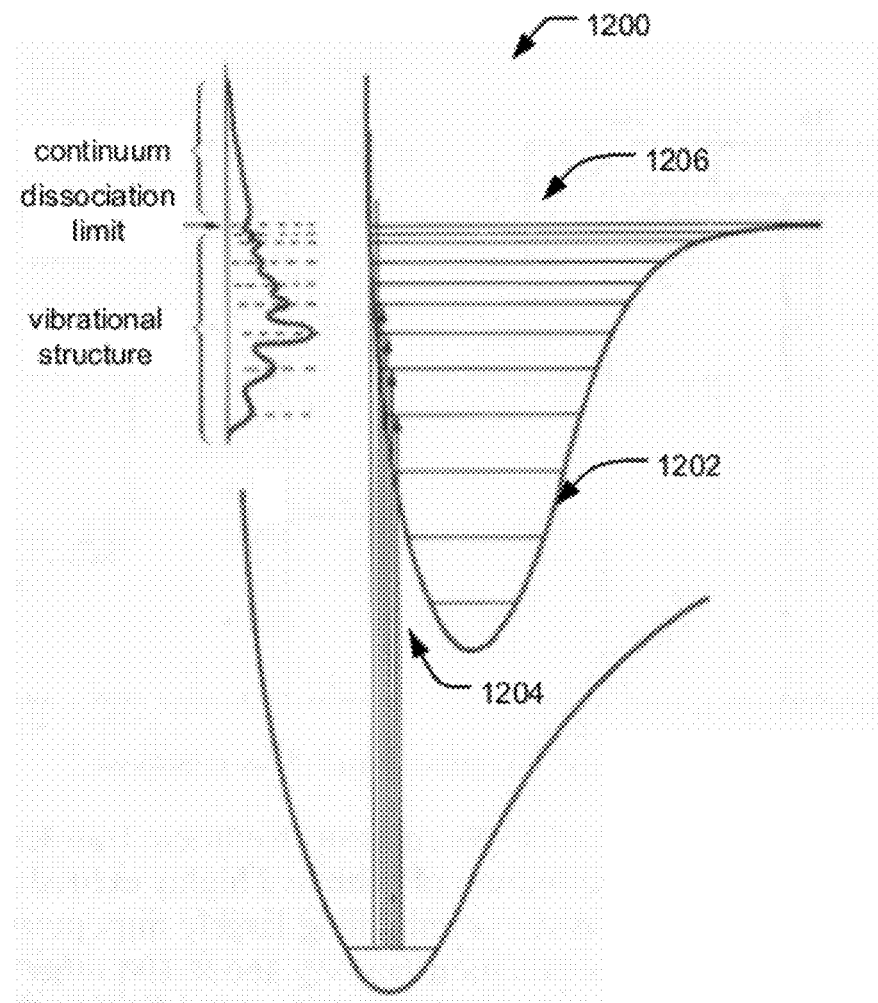
FIG. 12 is another graph that depicts the energy required to change the separation of the atoms that make a molecule.

FIG. 12 is an example graph 1200 that depicts the energy required to change the separation of the atoms that make a molecule such as, for example, n-C4. The separation ranges from the equilibrium lowest energy sate to the dissociation limit of the molecule. However, in other example implementations, the fluid sample may be composed of any number of different molecules and/or components (e.g., 2, 3, 4, etc.) and the graph 1200 may include multiple curves (e.g., 2, 3, 4, etc.) representing the dissociation of the different elements and/or components. As the dissociation limit of the molecule is reached, radials can be formed and may consecutively react to form new molecules as described therein.

Specifically, the graph 1200 includes a y-axis 1204 which represents an energy level (E), an x-axis 1206 which represents an internuclear distance (r), and a curve plot 1202 of the graph 1200 represents the energy of a molecular bond (e.g. a carbon-carbon bond) as a function of the distance between the atoms of the chemical bond. As the total energy (E) and the internuclear distance (r) increases, the molecule enters a relatively excited state until the molecule dissociates into fragments. At a relatively large internuclear distance, the molecule dissociates into two or more elements and/or components such as, for example, ions or free radicals. The ions may then migrate in the fluid under the action of an electrical field (e.g. the electrical filed generated by the electrodes 614 or 712 of FIGS. 6 and 7 respectively). Ions and free radical may recombine to form new molecules, or may reform the same molecule. Also, the generated ions or free radicals may recombine with ions or free radicals produced by the dissociation of other molecules (e.g., $O_2$) and may form carbon dioxide ($CO_2$) for example.

The change in energy (E) is equal to Planck's constant multiplied by the frequency, which is represented by the equation, $\Delta E = h\nu$, where (h) is Planks constant and ($\nu$) is the frequency. Thus, the change in energy (E) may be used to select the wavelength made available for ionizing, at least as a first approximation.

Although certain methods, apparatus, and articles of manufacture have been described herein, the scope of coverage of this patent is not limited thereto. To the contrary, this patent covers all methods, apparatus, and articles of manufacture fairly falling within the scope of the appended claims either literally or under the doctrine of equivalents.

What is claimed is:

1. A method of analyzing a downhole fluid, the method comprising:
    obtaining a sample of a downhole fluid;
    measuring a first parameter of the sample in a non-ionized state;
    ionizing at least a portion of the sample to decompose molecules having a relatively high molar mass into molecules having a relatively lower molar mass;
    measuring the ionized portion of the sample to determine a second parameter; and
    determining a property of the downhole fluid from the first and second parameters.

2. The method of claim 1 wherein ionizing the at least the portion of the sample comprises exposing the at least the portion of the sample to an ionizing energy.

3. The method of claim 2 wherein exposing the at least the portion of the sample to the ionizing energy comprises exposing the at least the portion of the sample to ultraviolet light.

4. The method of claim 2 further comprising exposing the at least the portion of the sample to the ionizing energy further comprises exposing the at least the portion of the sample to an electrical field.

5. The method of claim 1 wherein the molecules are hydrocarbon molecules.

6. The method of claim 1 wherein measuring the ionized portion of the sample comprises performing an optical measurement on the ionized portion of the sample.

7. The method of claim 1 wherein determining the property of the downhole fluid comprises comparing the second parameter of the ionized portion of the sample and the first parameter of the downhole fluid in the non-ionized state to reference data.

8. The method of claim 1 wherein the first and second parameters are indicative of the same physical property.

9. The method of claim 1 wherein determining a property of the downhole fluid comprises using a model of a molecular decomposition process to determine the parameter of the downhole fluid.

10. The method of claim 9 wherein determining a property of the downhole fluid comprises determining a change in a parameter of the sample due to the ionization of the sample and comparing the change to the model of the molecular decomposition process to determine the parameter of the downhole fluid.

11. The method of claim 10 wherein analyzing the ionized portion of the sample comprises monitoring a change in at least one of an electron spectrum or coloration of the at least the portion of the sample.

12. The method of claim 1 wherein the property of the downhole fluid is associated with a composition of the downhole fluid.

13. The method of claim 1 wherein at least one of the first and second parameter is associated with a concentration of at least one of, methane, ethane, or propane.

14. The method of claim 1 wherein the property of the downhole fluid is associated with a concentration of asphaltene.

15. The method of claim 1 wherein the downhole fluid is at least one of a wellbore fluid or a fluid extracted from a subsurface formation.

16. The method of claim 1 further comprising mixing a substance to the at least the portion of the sample.

17. The method of claim 16 wherein the substance is a diluent selected for changing a density of the at least the portion of the sample.

18. An apparatus to analyze a downhole fluid, comprising:
an ionizer to ionize at least a portion of a sample of the downhole fluid and to decompose molecules in the at least the portion of a sample having a relatively high molar mass into molecules having a relatively lower molar mass;
a fluid measurement unit to measure a characteristic of the sample of the downhole fluid;
a fluid measurement unit to measure a characteristic of the at least ionized portion of the sample;
a processing unit to determine a parameter of the downhole fluid based on the characteristic of the sample and the characteristic of the at least ionized portion of the sample.

19. The apparatus of claim 18 wherein the ionizer comprises a lightwave source.

20. The apparatus of claim 19 wherein the lightwave source comprises an ultraviolet light source.

21. The apparatus of claim 19 further comprising a plurality of electrodes to expose the at least the portion of the sample to an electric field.

22. The apparatus of claim 18 wherein the fluid measurement unit to measure a characteristic of the sample of the downhole fluid and the fluid measurement unit to measure a characteristic of the at least ionized portion of the sample are the same.

23. The apparatus of claim 18 wherein the processing unit is to determine the parameter of the downhole fluid by comparing the characteristic of the at least ionized portion of the sample to reference data.

24. The apparatus of claim 18 wherein the parameter of the downhole fluid is a concentration of a molecule present in the downhole fluid.

25. The apparatus of claim 24 wherein the parameter of the downhole fluid is associated with a concentration of at least one of, methane, ethane, or propane.

26. The apparatus of claim 18 wherein the downhole fluid is at least one of a wellbore fluid or a fluid extracted from a subsurface formation.

27. The apparatus of claim 18 further comprising one or more containers to hold one or more substance for mixing with the downhole fluid.

28. The apparatus of claim 18 further adapted for conveyance in a wellbore via at least one of a wireline and a drill pipe.

* * * * *